US009233217B2

(12) United States Patent
Jones

(10) Patent No.: US 9,233,217 B2
(45) Date of Patent: Jan. 12, 2016

(54) PERSONAL VAPOR DEVICE HAVING DISGUISED APPEARANCE

(71) Applicant: Jason S. Jones, Xenia, OH (US)

(72) Inventor: Jason S. Jones, Xenia, OH (US)

( * ) Notice: Subject to any disclaimer, the term of this patent is extended or adjusted under 35 U.S.C. 154(b) by 562 days.

(21) Appl. No.: 13/653,547

(22) Filed: Oct. 17, 2012

(65) Prior Publication Data

US 2014/0102463 A1    Apr. 17, 2014

(51) Int. Cl.
*A61M 15/06* (2006.01)
*A24F 47/00* (2006.01)

(52) U.S. Cl.
CPC .............. *A61M 15/06* (2013.01); *A24F 47/002* (2013.01); *A24F 47/008* (2013.01); *A61M 2202/0468* (2013.01); *A61M 2205/59* (2013.01); *A61M 2205/8206* (2013.01)

(58) Field of Classification Search
CPC ..... A24F 47/00; A24F 47/002; A24F 47/004; A24F 47/008; A61M 2205/59
See application file for complete search history.

(56) References Cited

U.S. PATENT DOCUMENTS

| 2,030,898 | A | * | 2/1936 | Robinson | 128/203.26 |
| 2,802,090 | A | * | 8/1957 | Katzman et al. | 392/337 |
| 7,832,410 | B2 | | 11/2010 | Hon | |
| D737,504 | S | * | 8/2015 | Chen | D27/183 |
| 2005/0016550 | A1 | | 1/2005 | Katase | |
| 2007/0272245 | A1 | * | 11/2007 | Ripple et al. | 128/205.28 |
| 2012/0255546 | A1 | * | 10/2012 | Goetz et al. | 128/202.21 |
| 2013/0199528 | A1 | * | 8/2013 | Goodman et al. | 128/203.26 |
| 2013/0239982 | A1 | * | 9/2013 | Meyer | A24F 13/00 131/328 |
| 2015/0076014 | A1 | * | 3/2015 | Kesten et al. | 206/261 |

FOREIGN PATENT DOCUMENTS

| CN | 2750680 Y | 1/2006 |
| WO | 2012/120487 A2 | 9/2012 |

OTHER PUBLICATIONS

By the-best-e-cigarette, Atomizer or Cartomizer—Which is the best?,Nov. 21, 2010 [downloaded on Jun. 10, 2015 from archive.org].*
Chinese Office Action dated Aug. 21, 2015.
English translation of Chinese Office Action dated Aug. 21, 2015.

* cited by examiner

*Primary Examiner* — Anthony Calandra
(74) *Attorney, Agent, or Firm* — Andrus Intellectual Property Law, LLP

(57) ABSTRACT

A personal vapor device having a disguised appearance is disclosed. The personal vapor device has an outer housing and removable lid that replicate the look of a conventional drinking container, such as a water bottle or drinking cup with a straw. An atomizing device, such as a cartomizer, is contained and concealed within the open interior of the outer housing. A mouthpiece extends through the removable lid and into the open interior. Atomized liquid from the cartomizer is delivered to the mouthpiece for delivery to the user. A power supply and a control circuit are contained within the open interior and, along with the atomizing device, are concealed within the outer housing. The disguised vapor device can be used without drawing attention to the user.

15 Claims, 6 Drawing Sheets

PERSONAL VAPOR DEVICE HAVING DISGUISED APPEARANCE

BACKGROUND

The present disclosure relates to a personal vapor device for delivering an atomized liquid to a user. More specifically, the present disclosure relates to a personal vapor device having a disguised appearance that delivers an atomized liquid to a user without drawing attention to the use of the device.

Various different types of smoking simulators have become increasingly popular. Smoking simulators deliver nicotine in an atomized mist and include a flavor that resembles that of cigarettes. Smoking simulators allow users to inhale nicotine without having to inhale the harmful chemicals and tar found in conventional tobacco cigarettes. Smoking simulators generally include an atomizing device that atomizes a supply of liquid including nicotine and a flavoring agent.

Most smoking simulators have a configuration that resembles the long, tubular shape of a cigarette. The shape of the smoking simulator, often referred to as an e-cigarette, allows the user to have an overall experience similar to smoking a cigarette while not delivering the carcinogenic substances created by burning tobacco and inhaling the smoke.

Although the shape of smoking simulators was selected to replicate a cigarette, users of e-cigarettes often suffer from the same anti-smoking stigmatism associated with actually smoking tobacco cigarettes. Further, the size and shape of conventional e-cigarettes make the use of e-cigarettes obvious and draws attention to the user. Since many users to do not wish to call attention to themselves, a desire exists for the creation of a personal vapor device that allows the user to use the vapor device without calling attention to himself or herself.

SUMMARY

The present disclosure relates to a personal vapor device that has a disguised appearance that replicates various different types of drinking containers. The use of the disguised vapor device allows the user to conceal the use and thus not draw attention to the use of the vapor device.

The disguised vapor device includes an outer housing having a main body and a removable lid. The outer housing and the removable lid define a concealed open interior. An atomizing device, such as a cartomizer, is contained within the open interior and is concealed from the exterior of the outer housing. The atomizing device is selectively operable to atomize a supply of liquid for delivery to the user.

The personal vapor device includes a mouthpiece that extends through the lid and into the open interior. The mouthpiece includes an open passageway that is in fluid communication with the cartomizer such that the atomized liquid from the cartomizer is delivered to the user through the mouthpiece. The mouthpiece can have various different appearances, such as but not limited to a flexible straw of a drinking cup or a drinking spout of a water bottle.

A power supply is contained within the open interior and is connected to a control circuit also contained within the open interior. The control circuit is connected to the atomizing device such that the control circuit can control the selective operation of the atomizing device. The power supply contained within the open interior of the outer housing provides power to the atomizing device and the control circuit.

In one embodiment of the disclosure, an activation button is positioned on the personal vapor device. Depression of the activation device begins operation of the cartomizer. Alternatively, various different types of activation devices could be utilized while operating within the scope of the disclosure. One contemplated embodiment utilizes a differential pressure sensor that senses reduced pressure around the distal end of the mouthpiece caused by the user to begin operation of the atomizing device.

The vapor device of the present disclosure has a disguised appearance. Although different appearances are contemplated, disguising the vapor device as a drinking container is a preferred appearance for the vapor device. In one embodiment, the vapor device has the look of a water bottle. In yet another alternate embodiment, the vapor device has the appearance of a drinking cup and straw.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Figure 1:
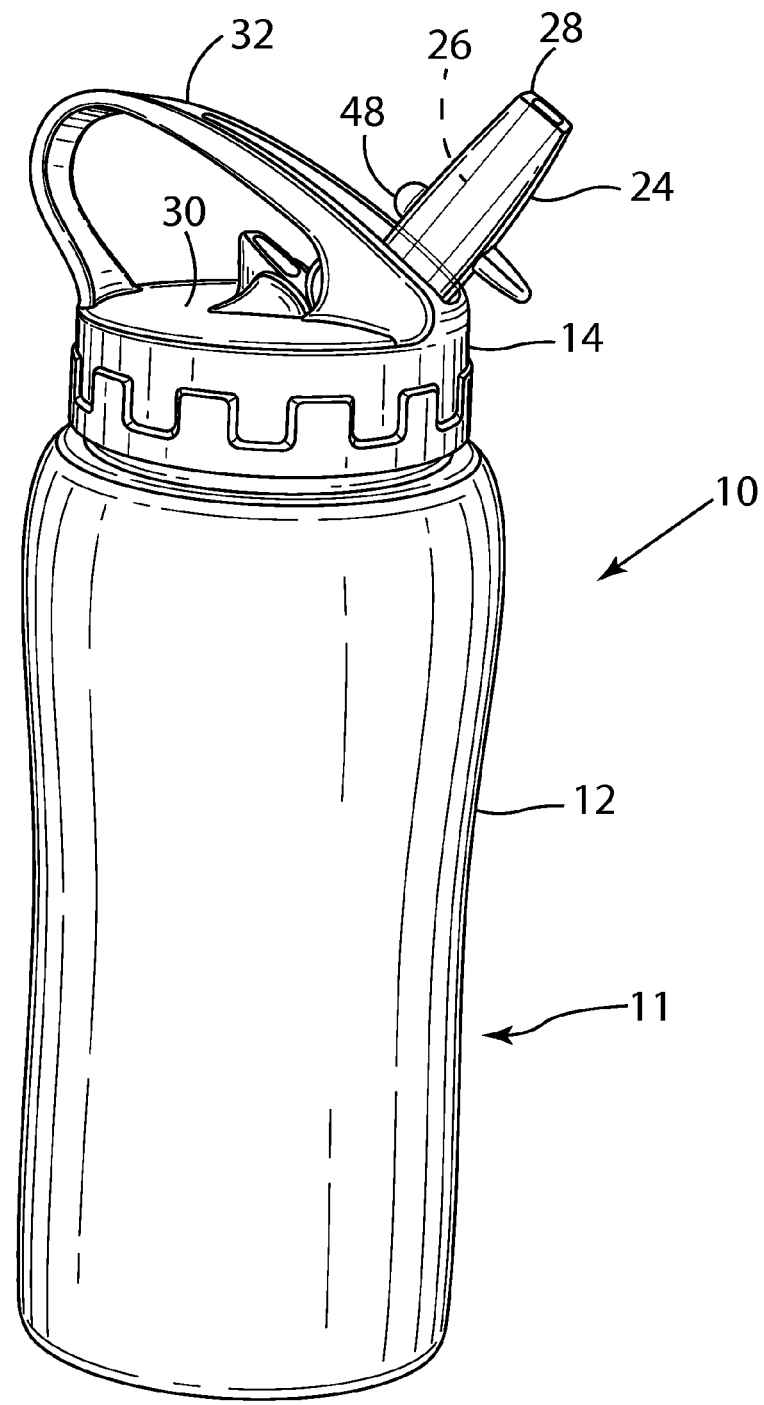
FIG. 1 is an isometric view of a first embodiment of the personal vapor device of the present disclosure.

FIG. 1 illustrates a first embodiment of a personal vapor device 10 constructed in accordance with the present disclosure. In the embodiment shown in FIG. 1, the personal vapor device has the general overall appearance of a common drinking container, namely a water bottle. Disguising the visual appearance of the personal vapor device 10 as a water bottle allows the user to utilize the personal vapor device 10 without drawing attention to the user.

Figure 2:
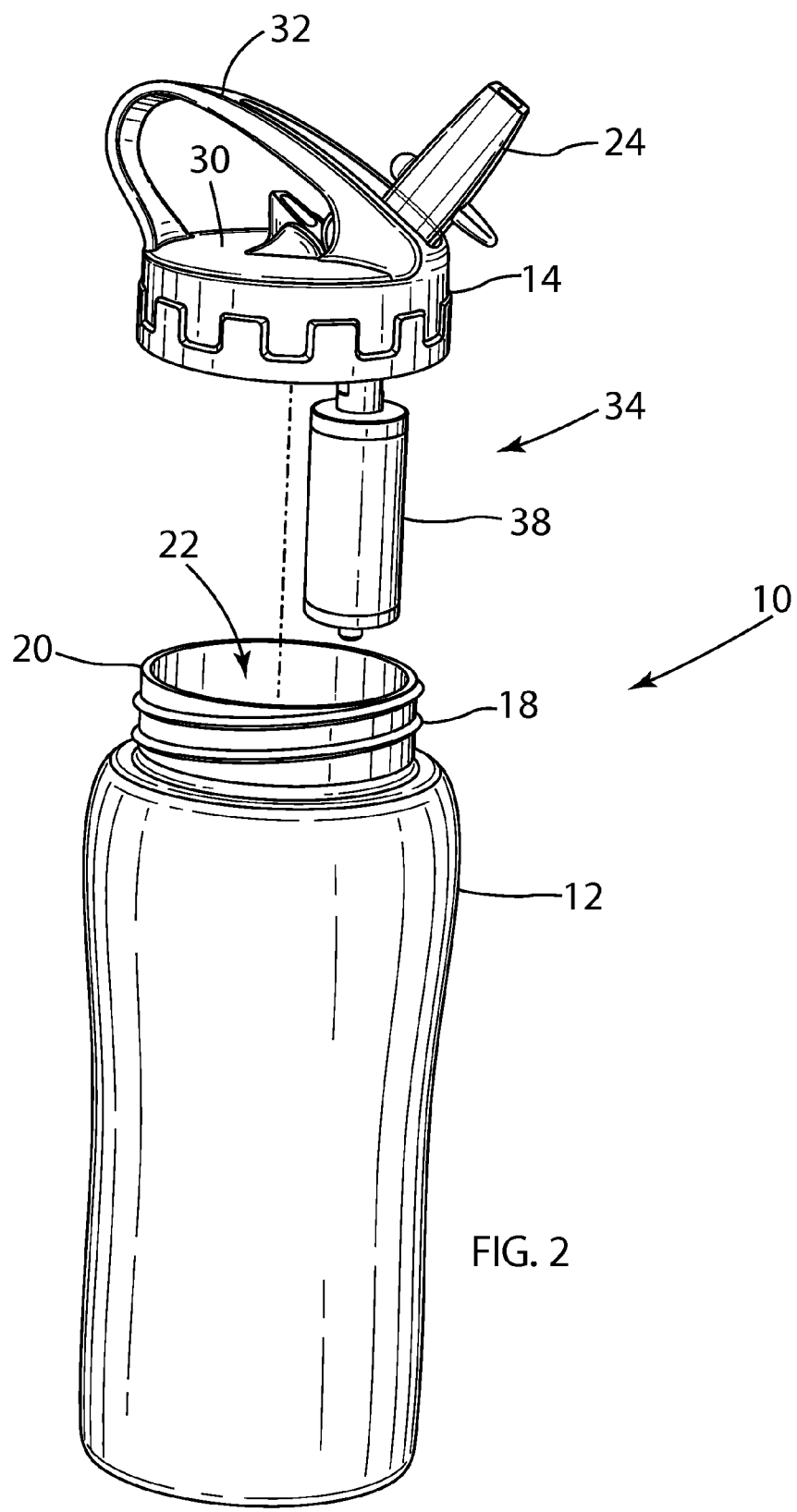
FIG. 2 is a partially exploded view of the personal vapor device of FIG. 1.
Figure 3:
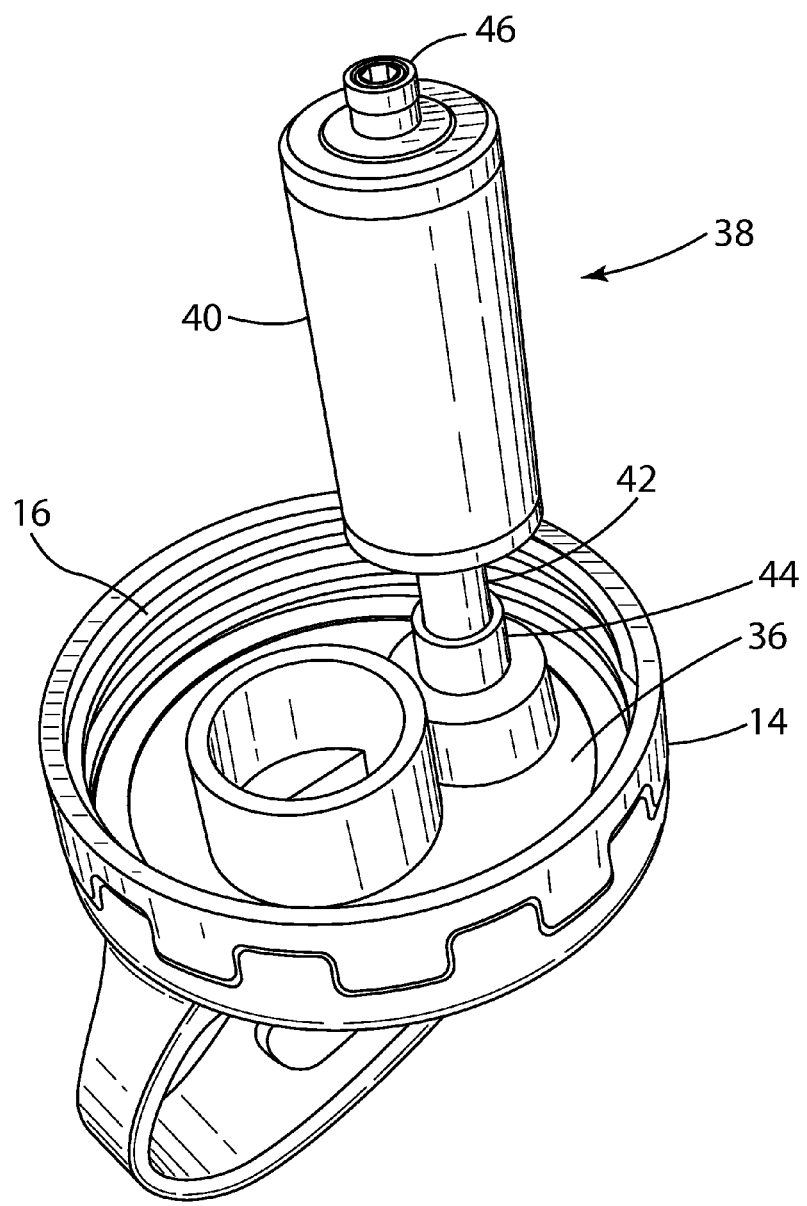
FIG. 3 is a bottom perspective view of the removed lid showing the attachment of a cartomizer to the lid of the vapor device.

In the embodiment shown in FIG. 1, the personal vapor device 10 includes an outer housing 11 having a main body 12 and a removable lid 14. As illustrated in FIGS. 2 and 3, the removable lid 14 includes a series of internal threads 16 that engage a series of external threads 18 formed on a neck 20 of the main body 12. The rotation of the removable lid 14 relative to the main body 12 allows the lid 14 to be securely attached to the main body 12 through the threaded interaction between the external threads 18 and the internal threads 16. The combination of the removable lid 14 and the main body 12 defines an open interior 22 of the personal vapor device 10.

As illustrated in FIGS. 1 and 2, the removable lid 14 includes a mouthpiece 24 having an internal passageway 26 that extends from the distal end 28 of the mouthpiece 24 through the top wall 30 of the lid 14 and into the open interior.

In the embodiment shown in FIGS. 1 and 2, the water bottle includes a top handle 32 that both replicates the general overall appearance of commonly available water bottles while also allowing a place for the user to hold the personal vapor device 10.

Referring now to FIGS. 2 and 3, the personal vapor device 10 includes an atomizing device 34 mounted to the inner surface 36 of the top wall 30 of the removable lid. When the removable lid 14 is attached to the main body 12, the atomizing device 34 is concealed within the open interior 22 defined by the main body 12 as shown in FIG. 1. In this manner, the vapor device 10 of the present disclosure is able to conceal the atomizing device 34 while maintaining the general overall appearance of a water bottle.

In accordance with the present disclosure, the atomizing device 34 can be one of many different devices that are operable to atomize a liquid into a fine mist for delivery to a user. As an example, the atomizing device could be an atomizer that is in fluid communication with a separate supply of liquid. An atomizer is typically connected to a power supply, such as a battery, which causes the atomizer to heat up and turn the liquid into a vapor. The vapor from a conventional atomizer is then delivered to the user.

Although an atomizer and separate liquid supply are contemplated as being within the scope of the present disclosure, in the preferred embodiment of the disclosure, the atomizing device is a cartomizer 38 is mounted to the inner surface 36 of the removable lid. A cartomizer is a commercially available device. Thus, the detailed construction and operation of the cartomizer are well known and thus not describe herein.

As shown in FIG. 3, the cartomizer 38 has a main body 40 and an outlet tube 42. The outlet tube 42 mounts to a receptacle 44 formed along the inner surface 36 of the lid 14. The receptacle 44 is coupled to the internal passageway of the mouthpiece to deliver the atomized mist from the outlet tube 42 of the cartomizer 38 to the user. A conventional cartomizer 38 includes an atomizer and a cartridge that are formed as a single unitary piece that connects to a power supply, such as a battery. A self-contained cartomizer 38 allows the user to simply replace the cartomizer 38 when the liquid supply has been depleted. It is contemplated that the cartomizer 38 could be either a refillable device or a disposable device while operating within the scope of the present disclosure. The cartomizer 38 includes a power supply end 46 that is used to connect the cartomizer 38 to a power supply, such as a storage battery.

Referring back to FIG. 1, the personal vapor device 10 includes an activation button 48 that can be selectively depressed by a user to begin operation of the cartomizer. After depression of the activation button 48, the cartomizer 38 is activated and begins to atomize the supply of liquid contained within the main body of the cartomizer.

Figure 4:
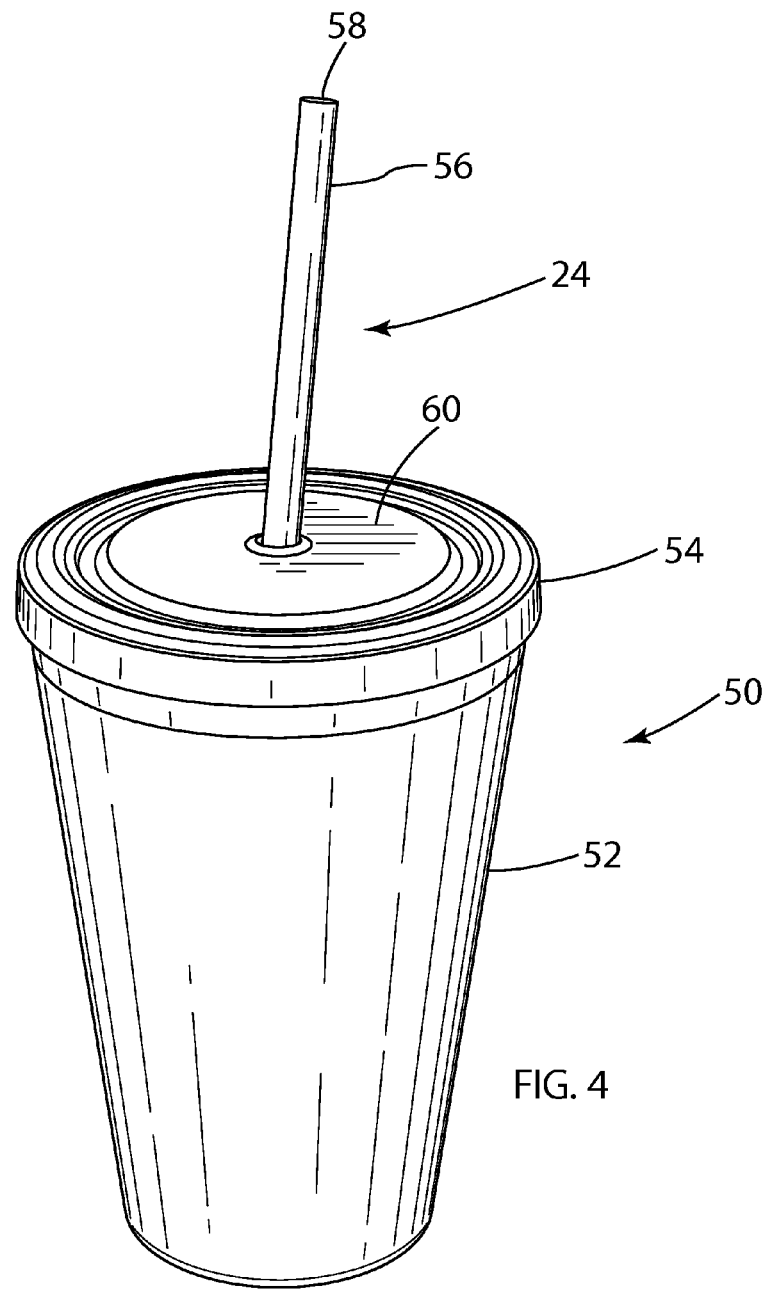
FIG. 4 is a perspective view of a second embodiment of the personal vapor device of the present disclosure.
Figure 5:
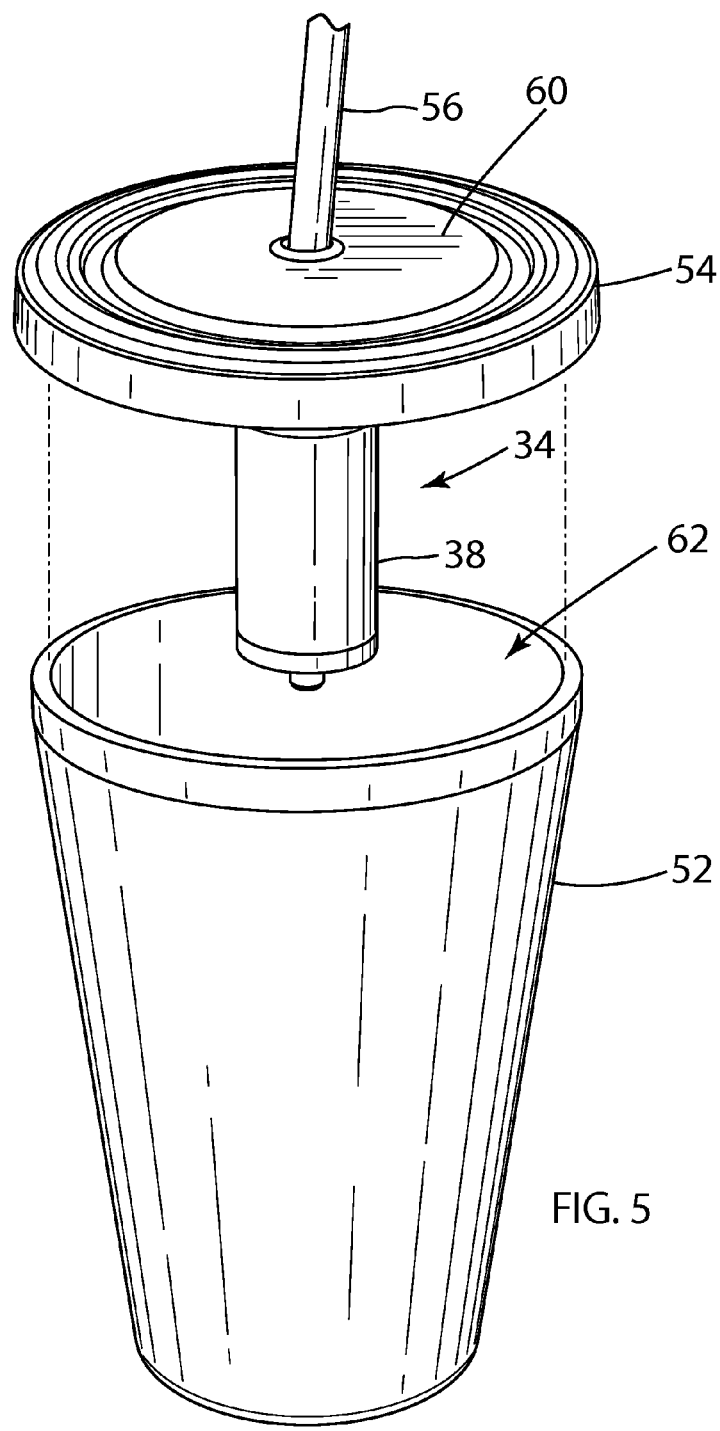
FIG. 5 is a partially exploded view of the personal vapor device of FIG. 4.

FIGS. 4 and 5 illustrate a second embodiment of the personal vapor device, which is referred to by reference numeral 50. The second embodiment of the personal vapor device is similar in operation to the first embodiment but instead of having the disguised appearance of a water bottle, the vapor device 50 takes the shape of a drink cup 52 having a removable lid 54. The removable lid includes the mouthpiece 24, which in the embodiment of FIGS. 4 and 5 takes the shape of a straw 56. The straw 56, like the drinking spout shown in the embodiment of FIGS. 1-3, extends from a distal end 58 through the top wall 60 of the removable lid 54. As illustrated in FIG. 5, the atomizing device 34, which may be an atomizer or a cartomizer 38, is mounted to an inside surface (not shown) of the removable lid 54. The removable lid 54 and the drinking cup 52 define an open interior 62 in a similar manner as described in the first embodiment of FIGS. 1-3.

Although a water bottle (FIGS. 1-3) and a drink cup with a straw (FIGS. 4-5) are two embodiments of the personal vapor device that allow the personal vapor device to be disguised, it is contemplated that various other configurations and appearances for the personal vapor device could be utilized. As an example, in the embodiment shown in FIG. 6, the personal vapor device has the appearance of a mug having a handle 64. The personal vapor device could have the appearance of various different drinking containers that include some type of enclosed interior and some type of mouthpiece for the user to receive the vapor created by the cartomizer 38.

Figure 6:
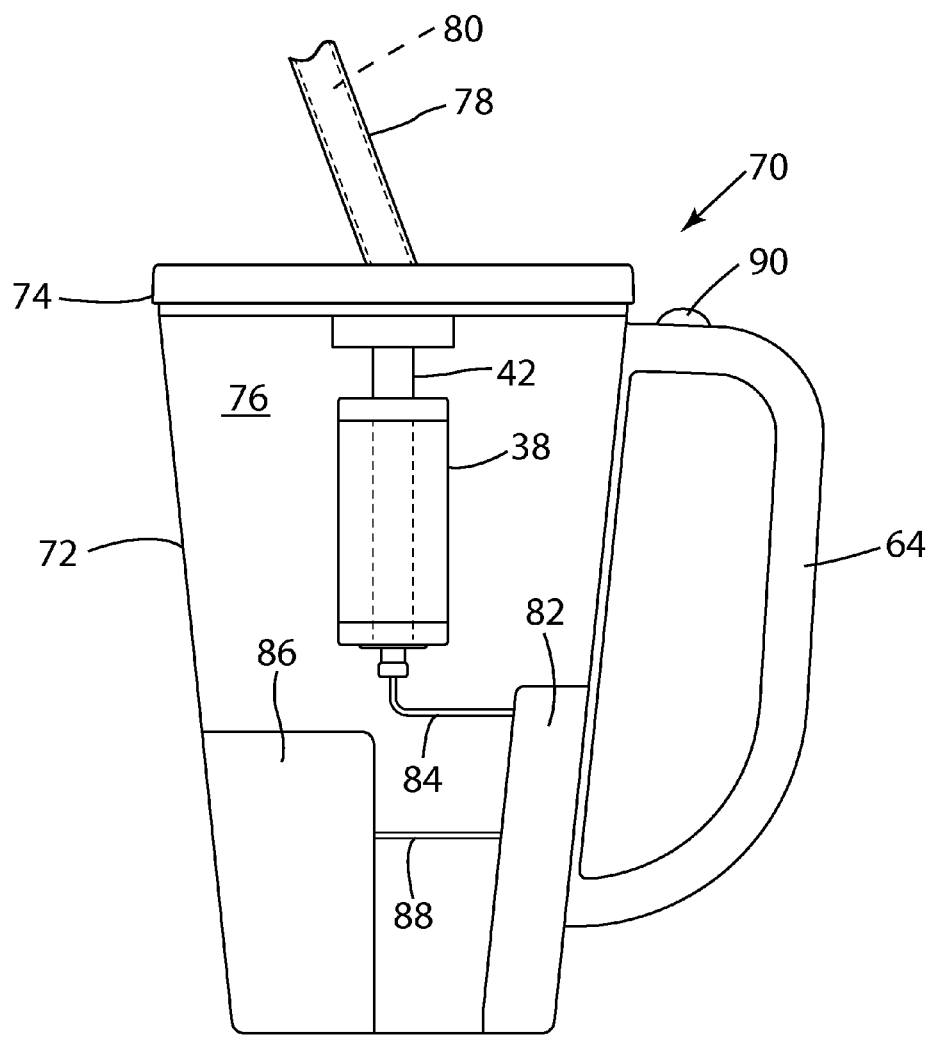
FIG. 6 is a schematic illustration of the components of the vapor device of the present disclosure.

FIG. 6 illustrates the general configuration of the personal vapor device, which is referred to by reference numeral 70 in FIG. 6. It should be understood that the representation of FIG. 6 also generally represents the first embodiment of FIGS. 1-3 and the second embodiment of FIGS. 4-5.

The personal vapor device 70 includes an outer housing including a main body 72 and a removable lid 74. The main body 72 and removable lid 74 define an open interior 76. The cartomizer 38 is shown having its outlet tube 42 mounted to the inner surface of the removable lid 74. A mouthpiece, such as the flexible straw 78, extends through the removable lid and is in fluid communication with the outlet tube 42. In this manner, liquid atomized by the cartomizer 38 can be delivered to a user through the open passageway 80 formed by the flexible straw 78.

As illustrated in FIG. 6, the cartomizer 38 is connected to a control circuit 82 by a control wire 84. The control circuit 82, in turn, is connected to a power supply 86. As can be understood in FIG. 6, both the control circuit 82 and the power supply 86 are contained within the open interior 76. The power supply 86 in the embodiment of FIG. 6 is a battery that is connected to the control circuit 82 through one or more wires 88. In this manner, the removable and replaceable power supply 86 can be used to power both the control circuit 82 and the cartomizer 38.

In the embodiment shown in FIG. 6, an activation button 90 is mounted to the external handle 64. When the user desires to operate the cartomizer 38, the user depresses the activation button 90, which sends a signal to the control circuit 82. When the control circuit receives the activation signal from the activation button 90, the control circuit activates the cartomizer 38 for a predetermined period of time to deliver the supply of vapor to the user. Although an activation button 90 is shown in FIG. 6, it is contemplated that various other types of activation devices could be utilized while operating within the scope of the present disclosure.

As one illustrative example, it is contemplated that the cartomizer 38 could include a differential pressure sensor that generates a signal to begin operation of the cartomizer. In such an embodiment, if the user inhales through the mouthpiece, the differential pressure sensor would sense the reduction in air pressure and the control circuit 82 would begin operation of the cartomizer 38. This alternate embodiment of the disclosure allows the user to "suck" on the end of the mouthpiece to begin operation of the cartomizer 38.

Although various embodiments of the atomizing device, outer housing and mouthpiece are shown and described, it should be understood that other embodiments are contemplated as being within the scope of the present disclosure. The disclosure conceals the atomizing device within an outer housing that has the appearance of another article, such as a drinking container, such that those in the vicinity of the user of the personal vapor device will not be able to identify the use of the personal vapor device.

I claim:
1. A personal vapor device, comprising:
an outer housing having a main body and a removable lid, the outer housing and the removable lid defining a concealed open interior;

a mouthpiece extending, through the lid and into the open interior;

a cartomizer including a self-contained supply of liquid mounted to an inner surface of the removable lid such that the cartomizer is removable from the open interior of the main body with the lid, wherein the cartomizer is concealed within the open interior and connected to the mouthpiece, wherein the cartomizer is operable to atomize the supply of liquid and deliver the atomized liquid through the mouthpiece; and a power supply contained within the open interior and coupled to the cartomizer to provide operating power to the cartomizer.

2. The vapor device of claim 1 wherein the outer housing, and the lid are a water bottle having a generally cylindrical main body and the mouthpiece is a drinking spout.

3. The vapor device of claim 1 wherein the outer housing and the lid are a drinking cup having a generally cylindrical main body and the mouthpiece is a flexible straw.

4. The vapor device of claim 1 further comprising a control circuit concealed in the open interior and coupled to the power supply and the cartomizer, wherein the control circuit controls the operation of the cartomizer.

5. The vapor device of claim 4 further comprising an activation button mounted to the exterior of the outer housing and coupled to the control circuit, wherein depression of the activation button activates the cartomizer.

6. The vapor device of claim 1 further comprising a control circuit concealed in the open interior and coupled to the power supply and the cartomizer, wherein the control circuit controls the operation of the cartomizer.

7. A personal vapor device having a disguised appearance for delivering an atomized liquid containing a dispersed drug, comprising:

an outer housing having a main body and a removable lid, the outer housing and the removable lid defining a concealed open interior;

a mouthpiece extending through the lid and into the concealed open interior; and a cartomizer mounted to an inner surface of the removable lid, wherein the cartomizer is concealed within the open interior and connected to the mouthpiece, wherein the cartomizer is removable from the main hod with the lid and is operable to atomize a supply of liquid and deliver the atomized liquid, through the mouthpiece.

8. The personal vapor device of claim 7 wherein the outer housing has an appearance of drinking container having a generally cylindrical main body.

9. The vapor device of claim 8 wherein the drinking, container is a water bottle and the mouthpiece is a drinking spout.

10. The personal vapor device of claim 8 wherein the drinking container is a drinking cup and the mouthpiece is a straw.

11. The personal vapor device of claim 8 further comprising a power supply contained within the open interior and connected to the cartomizer.

12. The personal vapor device of claim 11 further comprising a control circuit contained within the open interior and coupled to the power supply and the cartomizer, wherein the control circuit controls the operation of the cartomizer.

13. The personal vapor device of claim 12 further comprising an activation button mounted to an outer surface of the outer housing, wherein the control circuit activates the cartomizer upon depression of the activation button.

14. The personal vapor device of claim 7 wherein the cartomizer includes a supply of the liquid, wherein the liquid includes nicotine.

15. The personal vapor device of claim 7 wherein the mouthpiece includes an internal passageway that extends through the lid and into fluid communication with the cartomizer within the open interior, wherein the internal passageway delivers the atomized liquid to a user.

* * * * *

UNITED STATES PATENT AND TRADEMARK OFFICE
CERTIFICATE OF CORRECTION

| | | |
|---|---|---|
| PATENT NO. | : 9,233,217 B2 | Page 1 of 1 |
| APPLICATION NO. | : 13/653547 | |
| DATED | : January 12, 2016 | |
| INVENTOR(S) | : Jason S. Jones | |

It is certified that error appears in the above-identified patent and that said Letters Patent is hereby corrected as shown below:

IN THE CLAIMS

In column 6, claim 7, line 6, after "main", delete "hod" and insert --body--.
In column 6, claim 7, line 8, after "liquid" delete the ",".
In column 6, claim 8, line 10, after "of", insert --a--.

Signed and Sealed this
Nineteenth Day of April, 2016

Michelle K. Lee
*Director of the United States Patent and Trademark Office*